United States Patent
Nguyen et al.

(10) Patent No.: US 9,592,373 B2
(45) Date of Patent: Mar. 14, 2017

(54) FLUID CONNECTOR FOR ENDOSCOPE REPROCESSING SYSTEM

(75) Inventors: Nick N. Nguyen, Silverado, CA (US); Walter Francovich, Pierrefonds (CA); Philippe Conseil, Roxboro (CA)

(73) Assignee: Ethicon, Inc., Somerville, NJ (US)

( * ) Notice: Subject to any disclaimer, the term of this patent is extended or adjusted under 35 U.S.C. 154(b) by 825 days.

(21) Appl. No.: 12/998,459

(22) PCT Filed: Oct. 5, 2009

(86) PCT No.: PCT/US2009/059525
§ 371 (c)(1),
(2), (4) Date: Aug. 29, 2011

(87) PCT Pub. No.: WO2010/045055
PCT Pub. Date: Apr. 22, 2010

(65) Prior Publication Data
US 2011/0298209 A1    Dec. 8, 2011

Related U.S. Application Data

(60) Provisional application No. 61/196,713, filed on Oct. 13, 2008.

(51) Int. Cl.
*A61M 39/10*    (2006.01)

(52) U.S. Cl.
CPC ..... *A61M 39/10* (2013.01); *A61M 2039/1027* (2013.01)

(58) Field of Classification Search
CPC ...................... A61M 39/10; A61M 2039/1027
USPC ....... 285/338, 345, 109, 374, 379, 231, 233, 285/234
See application file for complete search history.

(56) References Cited

U.S. PATENT DOCUMENTS

| | | | | | |
|---|---|---|---|---|---|
| 1,492,521 | A | * | 4/1924 | Meyer | 285/374 |
| 2,996,317 | A | * | 8/1961 | Kibbie et al. | 277/607 |
| 3,682,503 | A | * | 8/1972 | Bloom | 285/345 |
| 3,719,375 | A | * | 3/1973 | Nordin | 285/339 |
| 3,899,200 | A | * | 8/1975 | Gamble | 285/93 |
| 4,116,476 | A | | 9/1978 | Porter et al. | |
| 4,483,510 | A | | 11/1984 | Palau et al. | |
| 4,637,378 | A | | 1/1987 | Sasa | |

(Continued)

FOREIGN PATENT DOCUMENTS

| | | |
|---|---|---|
| CN | 1872349 A | 12/2006 |
| EP | 1055860 A2 | 11/2000 |

(Continued)

OTHER PUBLICATIONS

International Search Report for International Application No. PCT/US2009/059525 mailed May 17, 2010, 3 pages.

(Continued)

*Primary Examiner* — James Hewitt
(74) *Attorney, Agent, or Firm* — K&L Gates LLP

(57) ABSTRACT

Coupling arrangements and connectors for establishing a substantially fluid-tight removable connection between a fluid port in a medical device such as an endoscope. Various embodiments of the connectors may be coupled to a fluid conduit that may be attached to a decontamination or reprocessing device used to flow fluid through corresponding channels in the medical device during the decontamination process.

12 Claims, 10 Drawing Sheets

(56) References Cited

U.S. PATENT DOCUMENTS

| | | |
|---|---|---|
| 4,753,268 A | 6/1988 | Palau |
| 4,981,469 A | 1/1991 | Whitehouse et al. |
| 5,167,220 A | 12/1992 | Brown |
| 5,234,417 A | 8/1993 | Parks et al. |
| 5,534,228 A | 7/1996 | Wesseler |
| 5,749,829 A | 5/1998 | Yokoi et al. |
| 5,806,832 A | 9/1998 | Larbuisson |
| 5,911,443 A * | 6/1999 | Le Quere .................. 285/3 |
| 6,095,971 A | 8/2000 | Takahashi |
| 6,158,829 A | 12/2000 | Nielsen |
| 6,273,478 B1 * | 8/2001 | Benett et al. ............ 285/346 |
| 6,345,844 B1 * | 2/2002 | Miyajima ............. F16L 37/02 285/231 |
| 6,454,314 B1 * | 9/2002 | Grosspietsch et al. ....... 285/319 |
| 6,485,684 B1 | 11/2002 | Mapson et al. |
| 6,840,548 B2 | 1/2005 | Lacroix |
| 6,958,017 B1 | 10/2005 | Toombs, Jr. |
| 6,986,736 B2 | 1/2006 | Williams et al. |
| 7,152,621 B1 | 12/2006 | Huetinck |
| 7,153,296 B2 | 12/2006 | Mitchell |
| 7,316,425 B2 | 1/2008 | Poder |
| 7,561,473 B2 | 7/2009 | Mokhlesi et al. |
| 7,604,262 B2 * | 10/2009 | Elflein et al. ............... 285/347 |
| 7,686,761 B2 | 3/2010 | Jackson et al. |
| 7,753,415 B2 | 7/2010 | Tiberghien et al. |
| 7,828,336 B2 | 11/2010 | Gammons |
| 7,837,646 B2 | 11/2010 | Eidinger et al. |
| 7,887,102 B2 | 2/2011 | Tiberghien et al. |
| 7,901,350 B2 | 3/2011 | Yamazaki |
| 8,113,548 B2 | 2/2012 | Gunderson |
| 8,146,883 B2 | 4/2012 | O'Hara |
| 2011/0298169 A1 | 12/2011 | Nguyen et al. |
| 2011/0298209 A1 | 12/2011 | Nguyen et al. |
| 2012/0007352 A1 | 1/2012 | Nguyen et al. |

FOREIGN PATENT DOCUMENTS

| | | | |
|---|---|---|---|
| EP | 1433410 A1 | 6/2004 | |
| EP | 1728466 A2 | 12/2006 | |
| EP | 1762172 A2 | 3/2007 | |
| GB | 2226861 A | 7/1990 | |
| GB | 2243890 A * | 11/1991 | ........... F16L 37/244 |
| JP | 2-209690 A | 8/1990 | |
| JP | 2-225898 A | 9/1990 | |
| JP | 5-49596 A | 3/1993 | |
| JP | 7-67938 A | 3/1995 | |
| JP | 8-112247 A | 5/1996 | |
| JP | 2000-70218 A | 7/2000 | |
| JP | 2002-71073 A | 3/2002 | |
| JP | 2004-202247 A | 7/2004 | |
| JP | 2005-58258 A | 3/2005 | |
| JP | 2006-55325 A | 3/2006 | |
| JP | 2006-149556 A | 6/2006 | |
| JP | 2007-289723 A | 11/2007 | |
| WO | WO 2006/062912 A1 | 6/2006 | |

OTHER PUBLICATIONS

International Preliminary Report on Patentability for International Application No. PCT/US2009/059525 issued Apr. 19, 2011, 6 pages.

* cited by examiner

FLUID CONNECTOR FOR ENDOSCOPE REPROCESSING SYSTEM

CROSS-REFERENCE TO RELATED APPLICATIONS

This application is a National Stage entry of International Application No. PCT/US2009/059525, entitled FLUID CONNECTOR FOR ENDOSCOPE REPROCESSING SYSTEM, filed on Oct. 5, 2009, which claims the benefit of U.S. Provisional Patent Application No. 61/196,713, entitled FLUID CONNECTOR FOR ENDOSCOPE REPROCESSING SYSTEM, filed on Oct. 13, 2008.

FIELD OF THE INVENTION

The present invention generally relates to connectors and, more particularly, to fluid connectors used in connection with reprocessing or decontamination systems for medical devices having one or more internal passageways that need to be cleaned and disinfected after use such as, for example, endoscopes.

BACKGROUND

In various circumstances, an endoscope can include an elongate portion, or tube, having a distal end which can be configured to be inserted into the body of a patient and, in addition, a plurality of channels extending through the elongate portion which can be configured to direct water, air, and/or any other suitable fluid into a surgical site. In some circumstances, one or more channels in an endoscope can be configured to guide a surgical instrument into the surgical site. In any event, an endoscope can further include a proximal end having inlets in fluid communication with the channels and, in addition, a control head section having one or more valves, and/or switches, configured to control the flow of fluid through the channels. In at least one circumstance, an endoscope can include an air channel, a water channel, and one or more valves within the control head configured to control the flow of air and water through the channels.

Decontamination systems can be used to reprocess previously-used medical devices, such as endoscopes, for example, such that the devices can be used once again. During the decontamination process of an endoscope, the air and water channels within the endoscope can be evaluated in order to verify that the channels are unobstructed. A variety of decontamination systems exist for reprocessing endoscopes. In general, such systems may include at least one rinsing basin, in which an endoscope that is to be cleaned and/or disinfected can be placed. The basin is commonly supported by a housing that supports a system of lines, pumps and valves for the purpose of feeding a cleaning and/or disinfecting agent to an endoscope which has been placed in a rinsing basin. Such devices also include a collection of lines, hoses, conduits or pipes that are coupled to the pumps and corresponding ports in the endoscope by releasable connectors. Such connectors must achieve a fluid-tight seal while attached to the endoscope, yet be easily releasable at the conclusion of the process. If the connector fails to achieve a fluid-tight seal, all of the endoscopes scope's lumens may never receive the disinfecting liquid medium to ensure that the inner surfaces of the lumen have been adequately disinfected.

While a variety of disconnectable fluid connectors have been designed over the years to couple the fluid-supplying lines from a reprocessing system to an endoscope lumen port, such connectors at times may not achieve a fluid-tight seal with the port or such connectors may be difficult to connect and detach from the port or ports. Other connectors are somewhat complex and may be difficult to manufacture and may easily be inadvertently disconnected from their respective ports on the endoscope.

Accordingly, there is a need for disconnectable connector for coupling fluid supply conduits to corresponding port or ports of an endoscope that may address some of the shortcomings of prior connectors.

The foregoing discussion is intended only to illustrate some of the shortcomings present in the field of the invention at the time, and should not be taken as a disavowal of claim scope.

SUMMARY

In at least one form of the invention, there is provided a connector for coupling a fluid conduit to an elongate fluid coupling member protruding from an endoscope. In various embodiments, the connector comprises a connector body that has an end wall and a bushing-receiving cavity therein. The end wall has a coupling opening therethrough sized to enable a portion of the elongate fluid coupling member to protrude therethrough. A flexible bushing may be received within the bushing-receiving cavity. The bushing may have a passage therethrough to enable at least a portion of the elongate fluid coupling member to be inserted therein. The flexible bushing may be sized relative to the bushing-receiving cavity to permit the bushing to flex therein about at least one attachment feature formed on the portion of the elongate fluid coupling member when the portion of the elongate fluid coupling member is inserted into the passage in the flexible bushing. The flexible bushing may further have at least one seal feature protruding from a portion of the bushing to establish another substantially fluid-tight seal between the bushing and the connector body.

In connection with other general aspects of various embodiments of the present invention, there is provided a coupling arrangement for conveying a fluid from a reprocessing device through a channel in an endoscope. In various embodiments, the coupling arrangement may comprise an elongate fluid coupling member that protrudes from the endoscope and is in fluid communication with the channel therein. The elongate fluid coupling member may have at least one retention feature protruding therefrom. The coupling arrangement may further include a fluid conduit that has a supply end that operably communicates with a source of fluid that is associated with the reprocessing device. The fluid conduit may further include a discharge end that is attached to a connector body. In various embodiments, the connector body may have an end wall and a side wall that protrudes from the end wall to define a cavity therein. A coupling opening may be provided through the end wall such that at least a portion of the elongate fluid coupling member may pass therethrough. A bushing may be received within the cavity. The bushing may have a passage therethrough that is sized to receive a portion of the elongate fluid coupling member therein such that the elongate fluid coupling member is removably retained within the bushing and a first substantially fluid-tight seal is established therebetween. The bushing may have at least one seal feature thereon for establishing a second substantially fluid-tight seal between the connector body and the bushing.

In connection with another general aspect of the present invention, there is provided a coupling arrangement for conveying a fluid from a reprocessing device through a channel in an endoscope. Various embodiments of the coupling arrangement may comprise an elongate fluid coupling member that protrudes from the endoscope and is in fluid communication with a channel therein. The elongate fluid coupling member may have a cylindrical body portion with an eccentric retention flange formed thereon. The coupling arrangement may further include a fluid conduit that has a supply end that operably communicates with a source of fluid that is associated with the reprocessing device. The fluid conduit may further have a discharge end that is coupled to a connector body. In various embodiments, the relative terms 'supply end' and 'discharge end' of the fluid conduit can refer to the ends of the fluid conduit in which fluid is supplied to and discharged from the fluid conduit, respectively, under the typical operating conditions of a reprocessing device. It certain circumstances, though, it is to be understood that the flow of fluid can be reversed through the fluid conduit and, in such circumstances, the relative terms 'supply end' and 'discharge end' become, for the sake of convenience, general reference terms as such reference terms would no longer correctly indicate the direction in which the fluid is flowing through the fluid conduit. In any event, a bushing seat may be seated within the connector body. The bushing seat may have a body portion and a flanged end. The body portion may have a bushing receiving passage therethrough. A flexible bushing may be received within the cavity. The bushing may have a passage therethrough that is sized to receive the body portion of the elongate fluid coupling member therein such that the body portion of the elongate fluid coupling member is removably retained within the bushing member and a first substantially fluid-tight seal is established therebetween. A seal is provided for establishing a second substantially fluid-tight seal between the bushing seat and the bushing.

This Summary is intended to briefly outline certain embodiments of the subject invention. It should be understood that the subject application is not limited to the embodiments disclosed in this Summary, and is intended to cover modifications that are within its spirit and scope, as defined by the claims. It should be further understood that this Summary should not be read or construed in a manner that will act to narrow the scope of the claims.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein.

Corresponding reference characters indicate corresponding parts throughout the several views. The exemplifications set out herein illustrate preferred embodiments of the invention, in one form, and such exemplifications are not to be construed as limiting the scope of the invention in any manner.

DETAILED DESCRIPTION

The following U.S. patent applications, which are each herein incorporated by reference and which are each being contemporaneously filed with the present application are commonly owned by the Assignee of the present application:

(1) U.S. patent application entitled Quick Disconnect Fluid Connector, Ser. No. 13/089,107; and (2) U.S. patent application entitled Endoscope Channel Separator, Ser. No. 13/089,106.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present invention is defined solely by the claims. The features illustrated or described in connection with one exemplary embodiment may be combined with the features of other embodiments. Such modifications and variations are intended to be included within the scope of the present invention.

Figure 2:
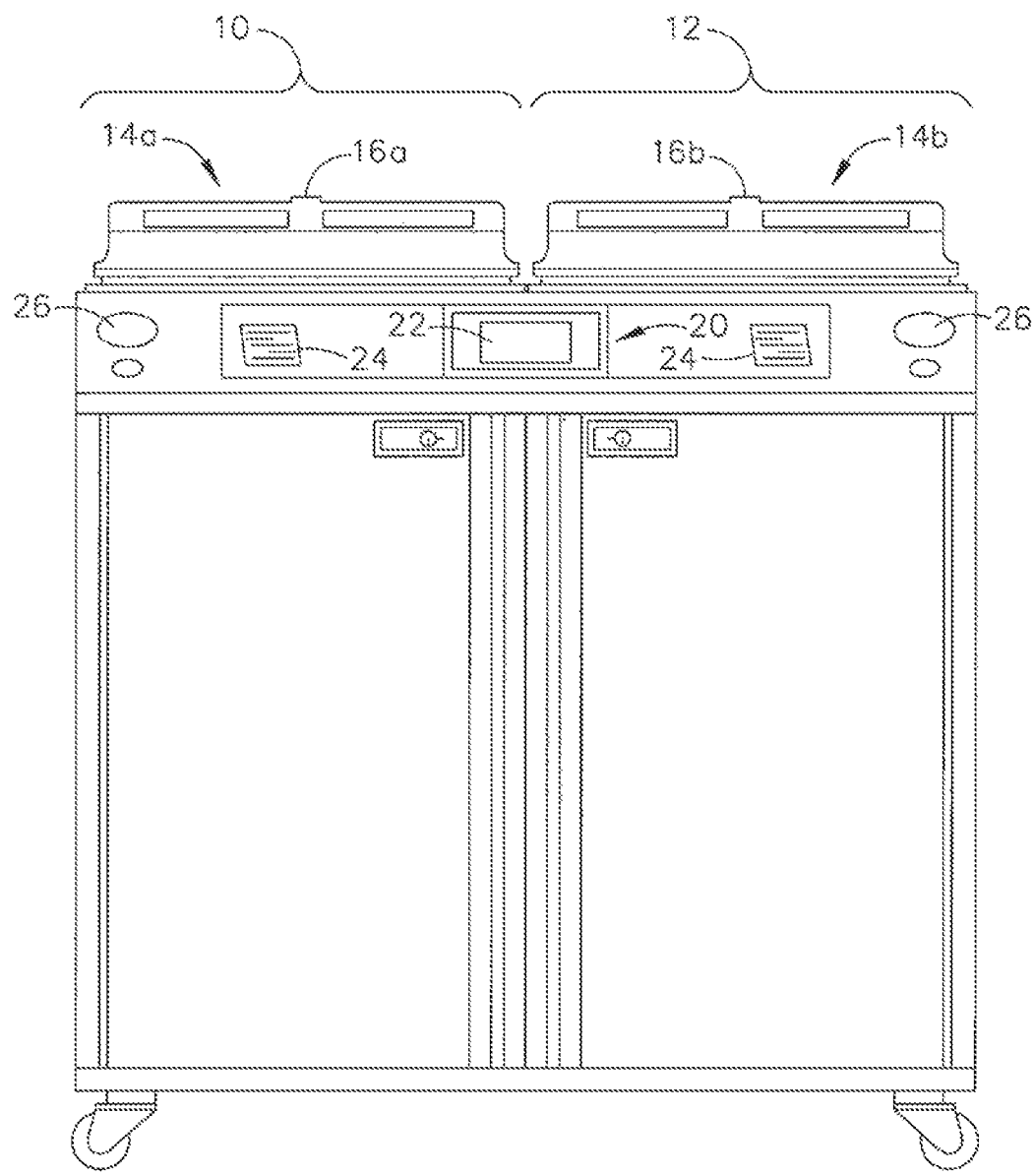
FIG. 2 is a front elevational view of a decontamination apparatus.

One embodiment of a decontamination apparatus is depicted in FIG. 2 which may be configured for decontaminating endoscopes and/or other medical devices. A variety of different systems and devices for decontaminating and reprocessing medical devices such as, for example, endoscopes are known in the art. Accordingly, the scope of protection afforded to the various connector arrangements of the present invention should not be limited to a particular processor or decontamination apparatus configuration.

In various arrangements, the decontamination apparatus can generally include one or more stations for decontaminating a medical device. In at least one arrangement, the decontamination apparatus can include a first station 10 and a second station 12 which can be at least substantially similar in all respects to provide for the decontamination of a medical device in series or two different medical devices simultaneously. In at least one arrangement, first and second decontamination basins, or chambers, 14a, 14b can receive the contaminated devices, wherein each chamber 14a, 14b can be selectively sealed by a lid 16a, 16b, respectively, preferably in a microbe-blocking relationship to prevent the entrance of microbes into the chambers 14a, 14b during the operation of the decontamination apparatus. In various arrangements, the lids can include a microbe removal or HEPA air filter, for example, for providing a flow of vented air therethrough.

A control system 20 can include one or more microcontrollers, such as a programmable logic controller (PLC), for example, for controlling the operation of the decontamination apparatus. Although one control system 20 is shown herein as controlling both decontamination stations 10, 12, each station 10, 12 can include a dedicated control system. In various arrangements, the decontamination apparatus can further include at least one visual display 22 configured to display decontamination parameters and machine conditions to an operator and, in addition, at least one printer 24 configured to print a hard copy output of the decontamination parameters which can be filed in a record-keeping system and/or attached to the decontaminated device or its storage packaging. In at least one arrangement, for example, the visual display 22 can be combined with a touch screen input device to facilitate the use of control system 20. In various arrangements, a keypad or the like can be provided for the input of decontamination process parameters and otherwise controlling the decontamination apparatus. Gauges, such as gauges 26, for example, can include pressure meters and/or any other suitable measuring device which can provide digital and/or analog output of decontamination or medical device leak testing data. Various leak testing devices and methods are disclosed in U.S. Pat. No. 6,986,736, entitled AUTOMATED ENDOSCOPE REPROCESSOR CONNECTION INTEGRITY TESTING, which issued on Jan. 17, 2006, the entire disclosure of which is hereby incorporated by reference herein.

Figure 3:
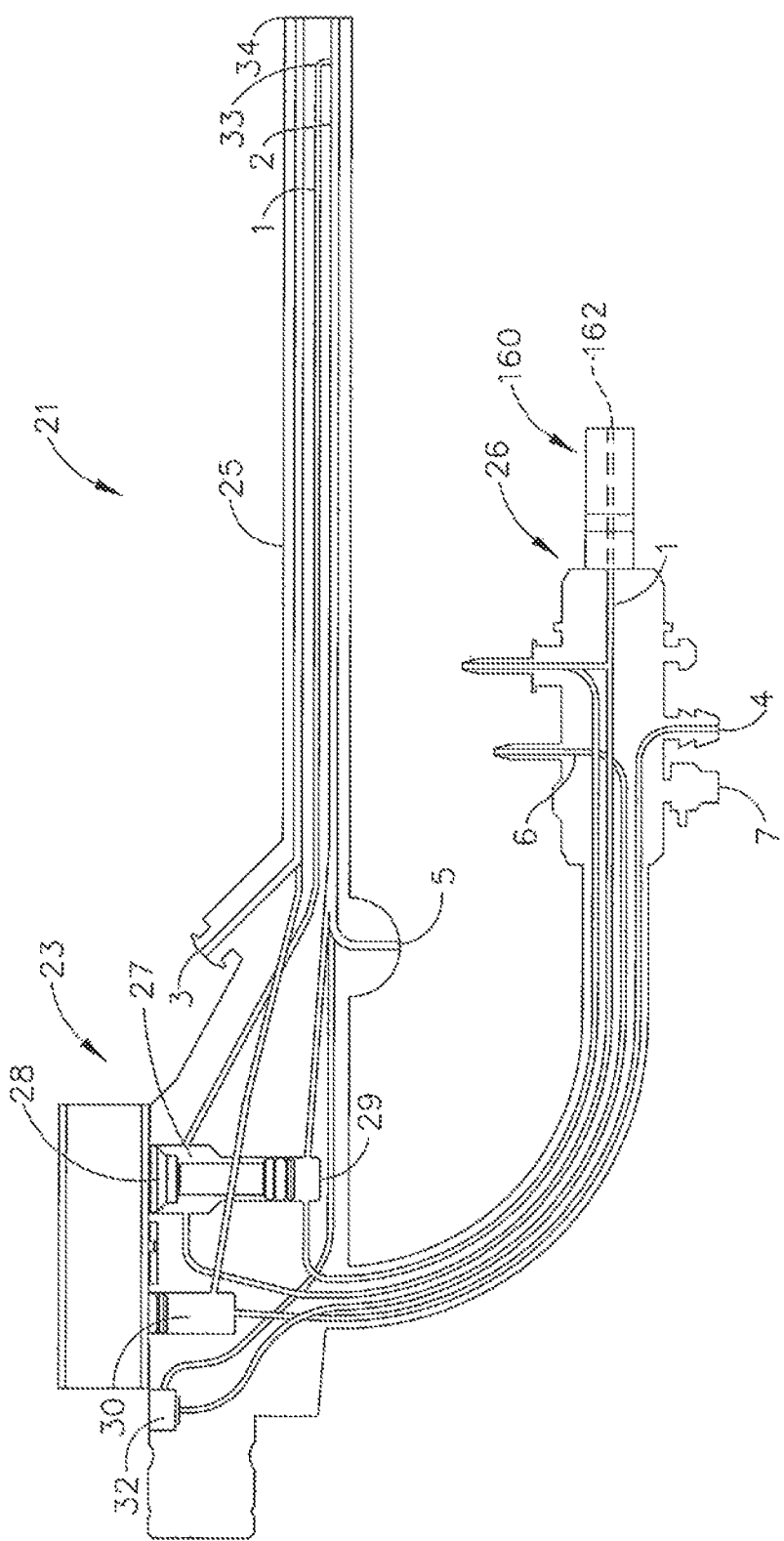
FIG. 3 is an elevational depiction of an endoscope, showing various channels lumens and passageways therein.

In various embodiments, referring to FIG. 3, an endoscope, such as endoscope 21, for example, can include elongate portion, or insertion tube 25 which can be configured to be inserted into the body of a patient through a trocar, for example. In at least one embodiment, endoscope 21 can further include proximal portion, or light guide section, 26, control head section 23, and one or more channels, or lines, for conveying a fluid. More particularly, an endoscope can include one or more channels extending therethrough which can be configured to convey a fluid, such as water, air, and/or carbon dioxide, for example, into a surgical site. As used herein, the term "fluid" may comprise liquid materials such as water, decontamination and sterilization liquids, etc., as well as materials in a vapor or gaseous state, such as, for example, air, carbon dioxide and various other gases. As used herein, the term "in fluid communication" means that a fluid-carrying or fluid-transporting member (e.g., pipe, hose, conduit, channel, etc.) is coupled to another fluid-carrying or fluid-transporting member so as to permit the fluid to flow or otherwise migrate from one member to the other.

Referring to FIG. 3, endoscope 21 can include a first channel 1 which is in fluid communication with a lumen 162 in a fluid coupling member 160 that may, for example, protrude from proximal end 26. Channel 1 may extend, for example, through at least a portion of control head section 23 and elongate portion 25, and to an outlet at distal end 34. In various embodiments, channel 1 can be configured to convey air to the surgical site, for example. Endoscope 21 can also include second channel 2 which can be configured to convey water from an inlet at proximal end 26, for example, through at least a portion of control head section 23 and elongate portion 25, and to an outlet at distal end 34. An endoscope 21 can further include additional channels, such as channel 4, for example, which can be configured to provide a vacuum, or suction, to a surgical site. An endoscope 21 can also include channel 6 for providing carbon dioxide. In at least one embodiment, an endoscope 21 can further include biopsy channel 3, for example, which can be configured to receive a surgical instrument therein such that the surgical instrument can be guided into the surgical site through the endoscope. In some embodiments, an endoscope 21 can further include a channel, such as channel 5, for example, which can be configured to convey a highly-pressurized jet of water that is discharged from distal end 34. In at least one embodiment, proximal end 26 can further include leak test connector 7 which can be configured to introduce a pressurized fluid and/or vacuum into the endoscope in order to inspect for leaks between the channels, for example.

In various embodiments, still referring to FIG. 3, control head section 23 can include valve chamber 32 which can be configured to receive a valve element therein such that the valve element can control the flow of carbon dioxide, for example, through the endoscope. In at least one embodiment, the valve element can comprise a stopcock, for example, which can be configured to allow carbon dioxide to flow through channel 6 when the stopcock is in a first, or open, position and prevent, or at least substantially prevent, the flow of carbon dioxide through channel 6 to distal end 34 when the stopcock is rotated into a second, or closed, position. Similarly, in various embodiments, control head section 23 can include valve chamber 30 which can be configured to receive a valve element therein which can be configured to control whether vacuum, or suction, can be communicated to distal end 34 through channel 4. In various embodiments, as discussed in greater detail below, control head section 23 can include a valve chamber, such as valve chamber 27, for example, comprising a first portion 28 in fluid communication with channel 1 and, in addition, a second portion 29 in fluid communication with channel 2. For the purposes of this application, any number of valves, channels, and/or any other suitable devices can be deemed to be in fluid communication with each other if a fluid can flow between the devices whether by pressure differential, gravity feed, and/or any other suitable manner.

In various embodiments, valve chamber 27 can be configured to receive a valve element having a seal configured to sealingly separate valve chamber 27 into portions 28 and 29. In at least one embodiment, the seal can be configured such that air flowing through channel 1 does not flow into, or at least substantially flow into, second portion 29, for example. Similarly, the seal can also be configured such that water flowing through channel 2 does not flow into, or at least substantially flow into, first portion 28. In various embodiments, although not illustrated, such a valve element can assist in sealingly separating two or more channels such that fluids flowing therethrough can be discharged from separate orifices in the distal end of an endoscope. In at least one alternative embodiment, referring to FIG. 3, channels 1 and 2 can be placed in fluid communication with one another at a location, such as location 33, for example, which is downstream from valve chamber 27 such that the air and water flowing through channels 1 and 2, respectively, can be discharged from the endoscope through a common orifice.

Figure 4:
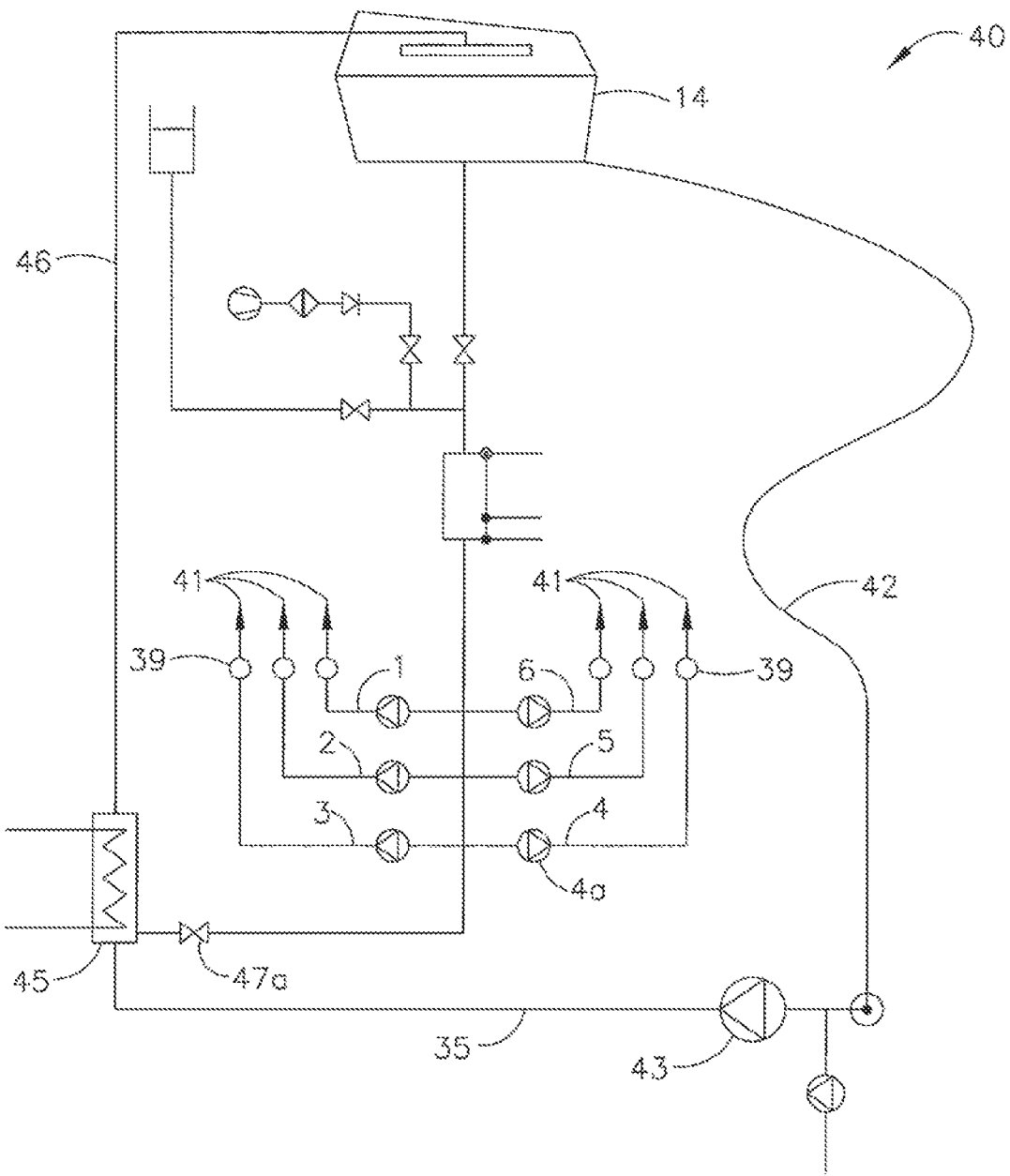
FIG. 4 is a schematic representation of a decontamination system that may be employed in connection with various embodiments of the present invention.
Figure 5:
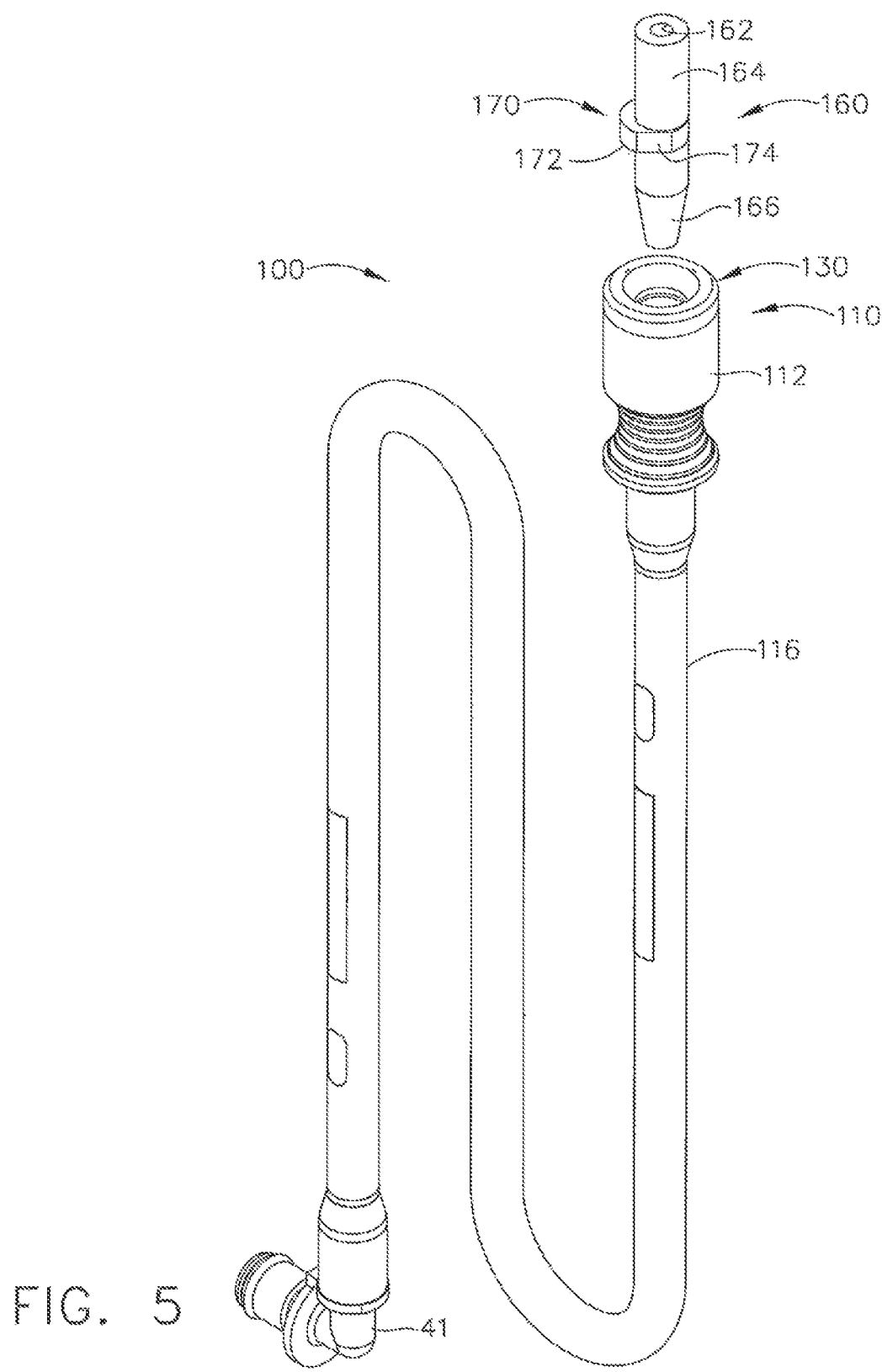
FIG. 5 is a perspective view of a coupling arrangement and elongate fluid coupling member of various embodiments of the present invention.

After an endoscope has been used, it can be reprocessed such that it can be used once again. In various circumstances, a decontamination apparatus, such as those described above, for example, can be utilized to decontaminate the endoscope and/or evaluate whether the endoscope has been properly decontaminated. In at least one circumstance, water, sterilant, and/or any other suitable fluid, can be flushed through one or more of the channels of the endoscope to remove debris, and/or any other foreign matter, which may have entered into the channels. In various embodiments, referring to FIG. 4, decontamination system 40 can include basin 14 which can be configured to receive at least a portion of an endoscope therein and, in addition, tube 42 which can, in at least one embodiment, be configured to receive at least a portion of, or be in fluid communication with, elongate portion 25 of the endoscope. In at least one embodiment, decontamination system 40 can further include circulation pump 43 which can be configured to circulate fluid from basin 14, for example, through endoscope 21 and/or tube 42, and into line 35. In certain embodiments, pump 43 can also be configured to push the fluid through heater 45 and into line 46 such that the fluid can be circulated back into basin 14, for example. In various embodiments, decontamination system 40 can further include valve 47a which can be configured to divert at least a portion of the fluid flowing within line 35 through the channels of the endoscope. More particularly, in at least one embodiment, decontamination system 40 can include six fluid connectors 41 which can be configured to receive fluid from line 35, wherein each of the six connectors 41 can be placed in fluid communication with one of the six channels of the endoscope, i.e., channels 1-6, for example, such that fluid, air, gas, etc. can flow therethrough.

Before, during, and/or after the endoscope has been subjected to a decontamination process, for example, the channels of the endoscope can be evaluated to determine whether debris, or any other foreign substance, remains in the channels. In various embodiments, referring to FIG. 4, a channel pump 4a associated with channel 4, for example, can be activated to motivate fluid through channel 4. In at least one such embodiment, a sensor, such as sensor 39, for example, can be configured to measure the flow rate of the fluid flowing through channel 4, wherein the flow rate measured by the sensor can be compared to an expected, or predicted, flow rate which represents the flow rate of the fluid when the channel is unobstructed. In various embodiments, the predicted flow rate through channel 4, for example, can be calculated in view of the parameters of channel pump 4a, the diameter, length, and/or various other properties of channel 4, and/or other features of the decontamination system. The predicted flow rate can also be empirically determined. In either event, in the event that the measured flow rate matches, or at least substantially matches, the expected flow rate, or is within a range of flow rates, for a given channel, the decontamination apparatus can convey to the operator that the existence of debris or a foreign substance within the channel is unlikely. In certain embodiments, sensors 39 can include pressure sensors which can be configured to detect the pressure of the fluid flowing through one or more channels. In the event that such a sensor 39 detects a fluid pressure that is above and/or below an expected pressure, or range or pressures, the decontamination apparatus can communicate to the operator that a foreign substance is present or that the endoscope, for example, is defective in some manner. In at least one such embodiment, the pressure sensors can, as a result, indirectly measure the rate of the fluid flowing through the channels.

In various embodiments, the measured flow rate and/or pressure of a fluid flowing through an endoscope channel does not have to exactly match the expected flow rate and/or pressure. In at least one embodiment, a channel can be deemed unobstructed if the measured flow rate is within an acceptable range relative to the expected flow rate, for example. In the event that the measured flow rate is not within the acceptable range, the decontamination apparatus can convey to the operator that the channel may be obstructed and that further investigation may be warranted. By way of example, if debris, or other foreign mater, is present within the channel, the debris may retard or reduce the flow rate of the fluid through the channel and the decontamination apparatus. Correspondingly, the debris or foreign matter may cause the pressure of the fluid to increase. In order to assist the operator in diagnosing the problem, the control system of the decontamination apparatus can convey information to the operator including which channel is being tested, the measured flow rate and/or pressure, and/or the percentage by which the measured value is different than the predicted value. In certain embodiments, a sensor can be configured to generate a series of signal pulses which correspond to the amount, or rate, of fluid flowing through a channel. For example, a sensor can generate signal pulses at a slower rate when the flow of fluid through or by the sensor is slower and, correspondingly, the sensor can generate signal pulses at a higher rate when the flow of fluid through or by the sensor is faster. In some circumstances, the rate in which the sensor produces signal pulses can be directly proportional to the rate in which the fluid is flowing through the channel. In at least one such embodiment, the decontamination apparatus can be configured to receive such signal pulses and, in view of such information, determine whether the fluid flow is appropriate.

Figure 6:
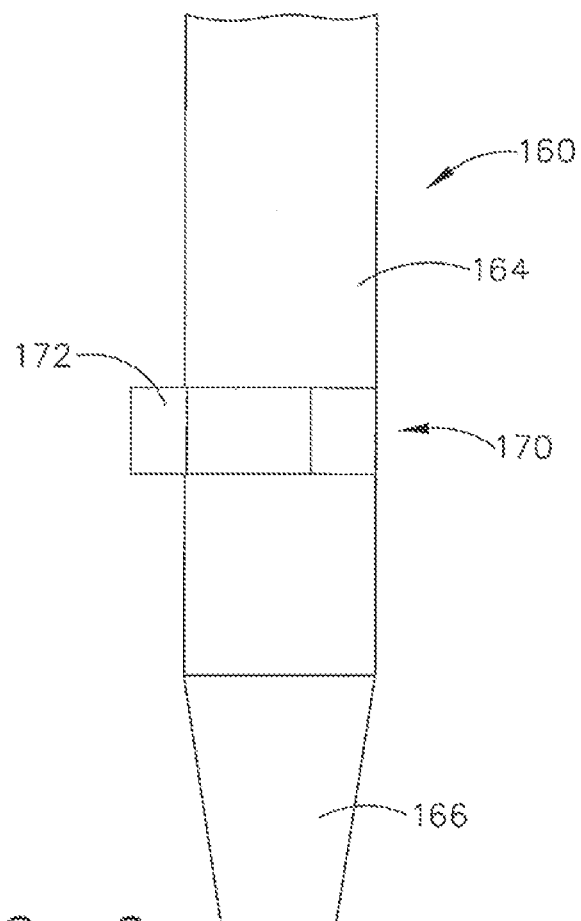
FIG. 6 is a partial side view of an elongate fluid coupling member of an embodiment of the present invention.
Figure 7:
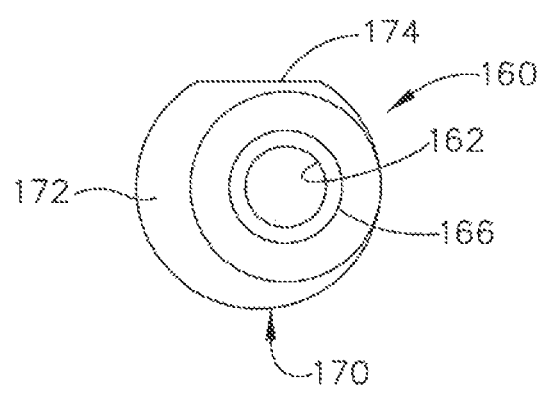
FIG. 7 is an end view of the elongate fluid coupling member of FIG. 6.
Figure 8:
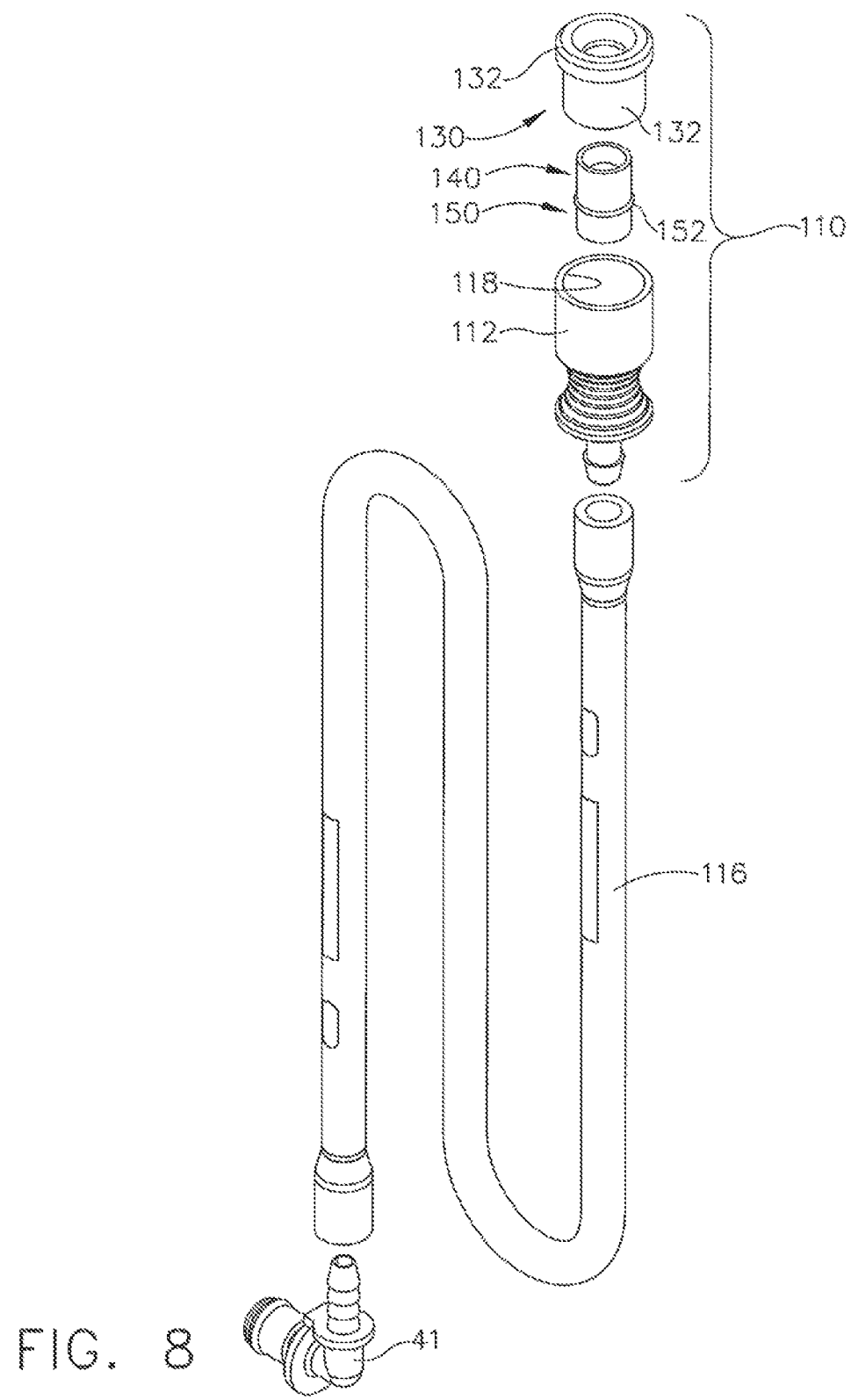
FIG. 8 is an exploded perspective view of the coupling arrangement depicted in FIG. 5.
Figure 10:
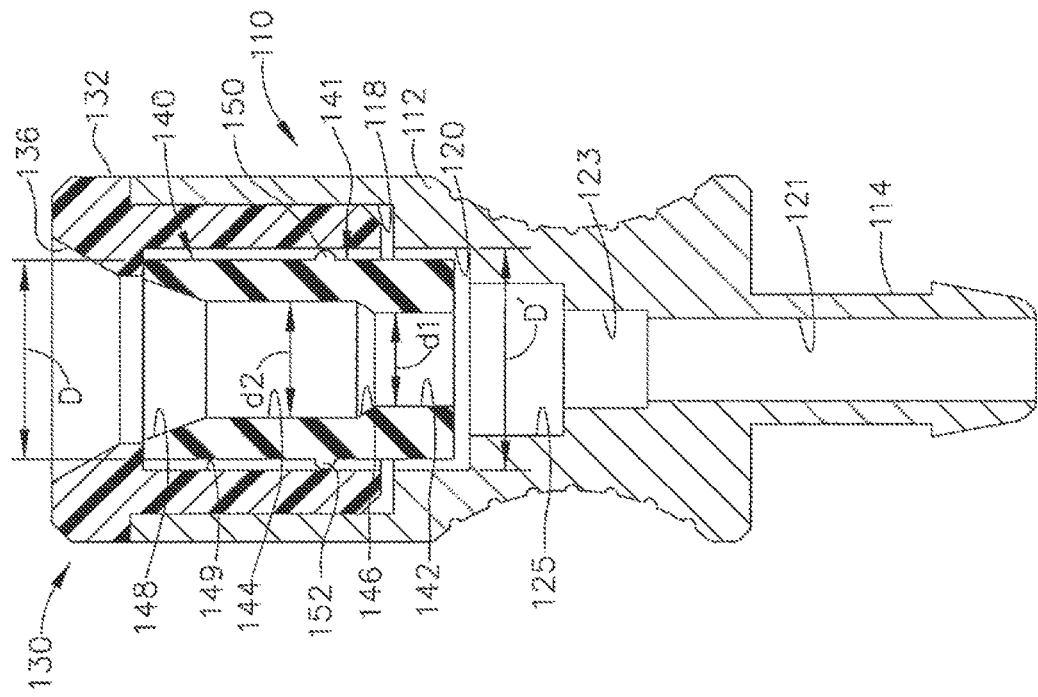
FIG. 10 is a cross-sectional view of the connector of FIG. 9 with a bushing embodiment of the present invention seated therein.
Figure 9:
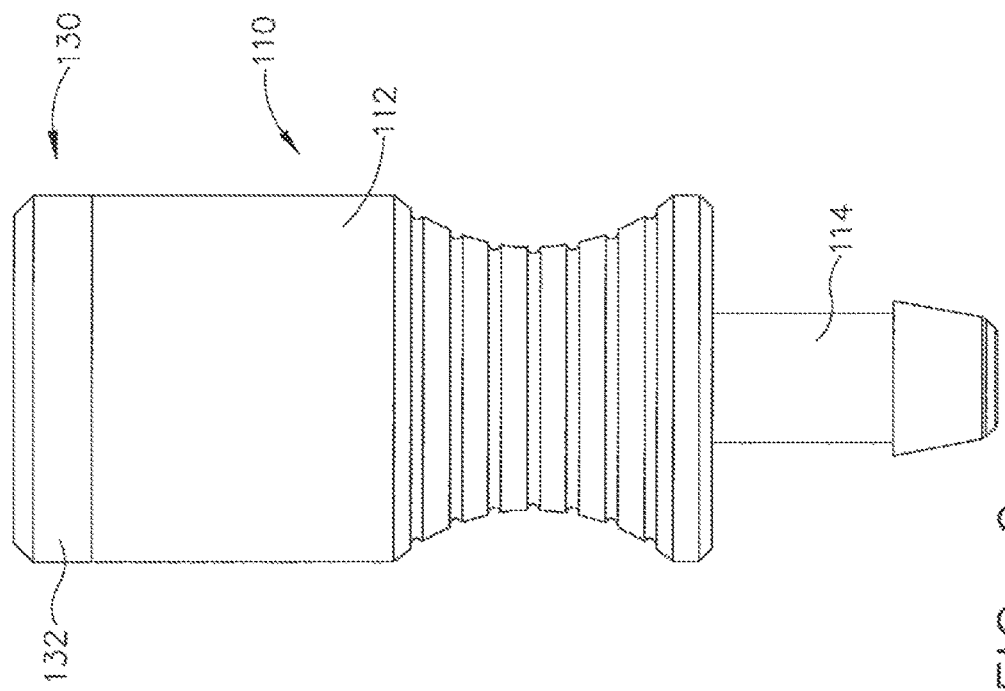
FIG. 9 is a side view of a connector embodiment of the present invention.

Referring now to FIGS. 1, 3 and 5-11, there is shown a coupling arrangement generally designated as 100 for conveying a fluid such as, for example, air from the decontamination device 40 to an elongate fluid coupling member 160 that protrudes from the proximal end 26 of the endoscope 21 and which is in fluid communication with channel 1 therein. See FIG. 3. As can be most particularly seen in FIGS. 5-7, the elongate fluid coupling member 160 has a lumen or passage 162 therethrough that is adapted to communicate with channel 1 within the endoscope 21. In various embodiments, the elongate fluid coupling member 160 may be fabricated from any suitable material, such as stainless steel 316, for example, and can be attached to the proximal end 26 of the endoscope 21 by various known fastener arrangements. As can be seen in FIGS. 6 and 7, the elongate fluid coupling member 160 may have a cylindrical body portion 164 and a discharge end 166. In various embodiments, the cylindrical body portion may have substantially circular cross-sectional shape. See FIG. 7. The discharge end 166 may be tapered or frusto-conical in shape to facilitate insertion and alignment of the coupling member 160 within connector 110 in the manner described in further detail below.

As can also be seen in FIGS. 6 and 7, the elongate fluid coupling member 160 may be further provided with at least one retention feature, such as retention feature 170, for example, that protrudes from the body portion 164. In certain embodiments, a retention feature can comprise at least one enlarged portion and/or at least one enlarged diameter which is larger than body portion 164, for example, and which extends along the length of body portion 164. In various embodiments, retention feature 170 may comprise a retention flange 172. In some embodiments, for example, the retention flange 172 may be eccentrically formed relative to the body portion 164 as can be most particularly seen in FIG. 7. For example, the retention flange 172 may be formed or positioned relative to the body portion 164 such that it is not coaxially aligned therewith. In addition, in some embodiments, the eccentrically aligned retention flange 172 may have at least one flattened area or surface 174 formed thereon. In at least one embodiment, flat surface 174 can comprise a locking feature or surface which can be used to affix fluid coupling member 160 within connector 110, such as in a twist to lock configuration, for example, wherein, in certain circumstances, flat surface 174 can facilitate the insertion of fluid coupling member 160 into the connector 110 while not compromising the frictional fluid-tight seal established therewith. In various embodiments, a retention flange, similar to retention flange 172, for example, can include a first flattened area or surface 174 on one side of the retention flange and a second flattened area or surface 174 on the opposite side of the retention flange. In at least one such embodiment, the first and second flattened areas or surfaces 174 can be parallel, or at least substantially parallel, to one another. In certain embodiments, the retention feature 170 may have other suitable shapes as well as more than one retention member may be employed without departing from the spirit and scope of the present invention. In at least one embodiment, a fluid coupling member can comprise a body portion similar to body portion 164, for example, and a retention feature similar to retention feature 170 and flange 172, for example, wherein the retention flange can be concentrically formed or positioned, or at least substantially concentrically formed or positioned, relative to the body portion. In at least one such embodiment, body portion 164 can comprise a circular, or at least substantially circular, profile or perimeter and, in addition, retention feature 170 can comprise a circular, or at least substantially circular, profile or perimeter, wherein, although not illustrated, the circular profiles defined by body portion 164 and retention feature 170 can be concentric, or at least substantially concentric. In some such embodiments, the retention feature can also comprise a flat surface or portion similar to flat surface 174, for example, for facilitating a twist to lock connection between the fluid coupling member and a connector, for example, and for facilitating the insertion of the fluid coupling member into a bushing.

In various embodiments, the connector 110 may comprise a body portion 112 that may be configured as shown in FIGS. 1 and 8-11. The body portion 112 may be fabricated from any suitable material, such as stainless steel 316, for example, and have a hose barb 114 or other connector formation integrally protruding therefrom for attachment to a fluid conduit 116 in various known manners. The fluid conduit 116 may comprise a flexible hose or tube and may also have a conventional hose fitting 41 attached thereto to facilitate coupling of the fluid conduit 116 to the decontamination device as was discussed above. The connector 110 may further include a rigid bushing seat 130 that has a body portion 132 sized to be received in a cavity 118 provided in the body portion 112 of the connector 110. The bushing seat 130 may have a flanged end 132 and can be fabricated from any suitable material, such as Acetal, for example.

Figure 1:
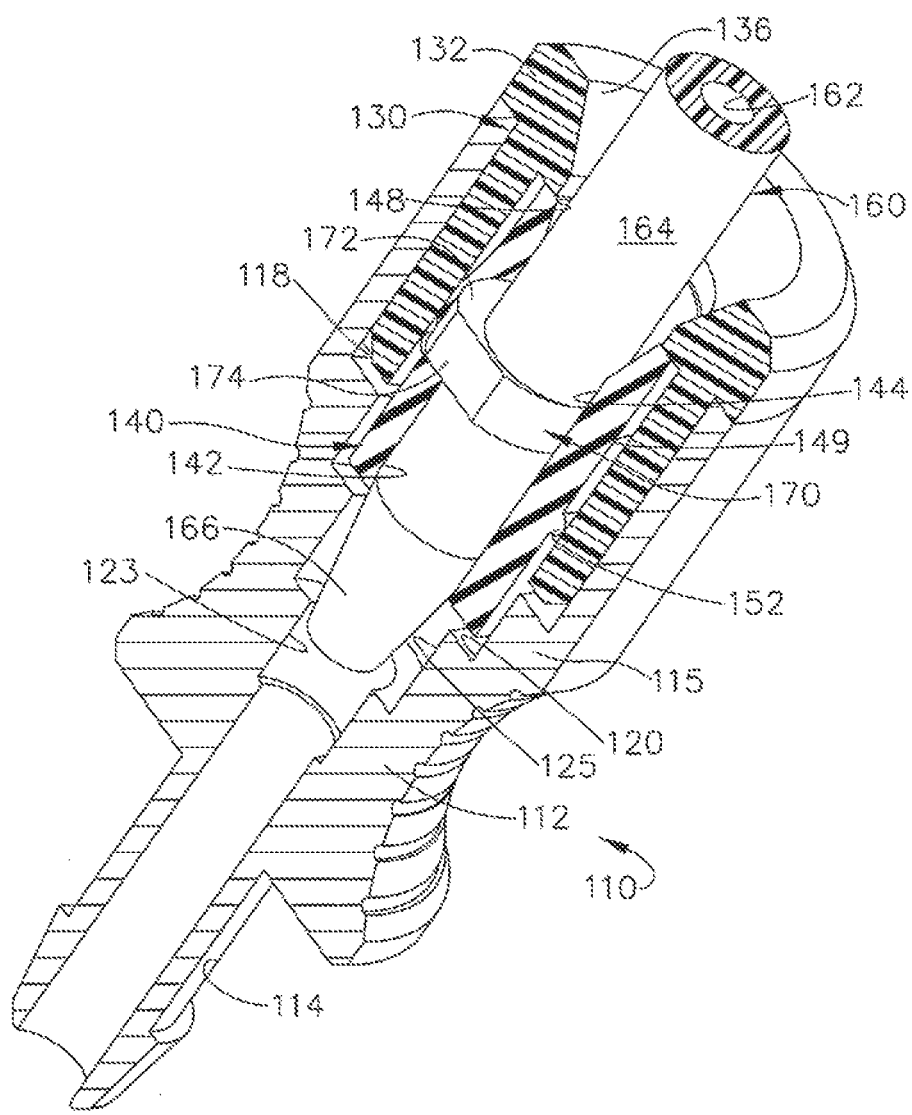
FIG. 1 is a perspective view of the cross-sectional depiction of FIG. 11.

As can be seen in FIG. 1, the body portion 112 may also be provided with a bushing cavity 120 therein for receiving a portion of a bushing 140 therein. In particular, a substantially flexible bushing 140 may be supported within the bushing seat 130 and extend into a bushing cavity 120 which is defined by a side wall 115 of the connector body 112. In various embodiments, the bushing 140 may be fabricated from a silicone material that permits the bushing 140 to flex around the retention flange 172 and establish a substantially fluid-tight seal with the elongate fluid coupling member 160 as will be discussed in further detail below. In at least one embodiment, the bushing 140 could be fabricated from approximately 50 Durometer Shore A silicone, for example.

In various embodiments, the bushing 140 may be provided with an alignment passage 142 that serves to properly align the end 166 of the elongate coupling member 160 with coaxially aligned passage portions 121, 123, 125 in the body portion 112 of the connector 110. See FIG. 10. Also in various embodiments, the bushing 140 may have a central passage portion 144 that is larger in diameter than the diameter of the alignment passage 142. For example, the alignment passage 142 may have a diameter "d1" of approximately 3.20 mm, for example, while the central passage portion 144 may have a diameter "d2" of approximately 4.50 mm, for example. To assist with the insertion of the end 166 of the elongate fluid coupling member 160 into the alignment passage 142 from the central passage portion 144, a tapered wall portion 146 may be provided between the passage portions 142, 144 as can be most particularly seen in FIG. 10. Similarly, to facilitate easy insertion of the end 166 of the elongate fluid coupling member 160 into the bushing 140, a tapered passage portion 136 may be provided through the flanged end 132 of the bushing seat 130 and another tapered passage portion 148 may be provided in the bushing 140. As can also be seen in FIGS. 1, 8, 10 and 11, a seal feature 150 may be provided on the bushing 140 to establish a substantially fluid-tight seal between the bushing 140 and the bushing seat 130. In various embodiments, the seal feature 150 may comprise an annular ring 152 that protrudes outward from the perimeter 141 of the bushing 140. In various embodiments, the annular ring 152 may be integrally formed in the perimeter of the bushing 140. In other embodiments, however, the seal feature 150 could comprise an O-ring or O-rings on the bushing 140 and or seated in a portion or portions of the bushing seat 130, for example, without departing from the spirit and scope of the present invention.

Use of the bushing seat 130 may, among other things, facilitate ease of manufacture and installation of the bushing 140 in the connector 110. For example, the bushing 140 may be installed in the body portion 112 of the connector 110 prior to installing the bushing seat 130. Other embodiments, however, may lack a bushing seat, such that the bushing is supported directly within the connector body and is configured to establish a substantially fluid-tight seal therewith. In the depicted embodiment, the body portion 132 of the bushing seat 130 may be sized relative to the cavity 118 such that it may be retained therein by a frictional fit. Thus, once the bushing 140 has been inserted into the body portion 112, the bushing seat 130 may be pressed into the cavity 118 of the body portion 112 to retain the bushing 140 therein. Such arrangement also affords the user with the opportunity to replace the bushing 140 should it become inadvertently damaged or compromised. However the bushing seat 130 may be fastened to the body portion of the connector 112 by other suitable fastener arrangements.

Figure 11:
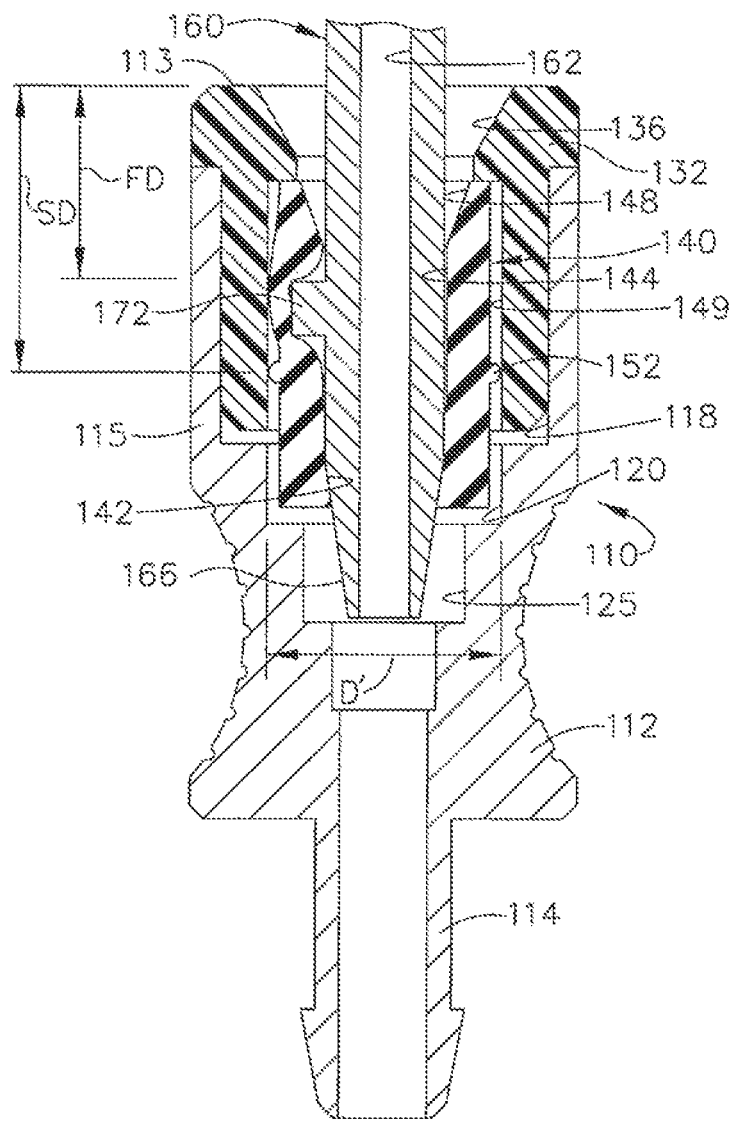
FIG. 11 is a cross-sectional view of the connector of FIGS. 9 and 10 with the elongate fluid coupling member of FIGS. 6 and 7 inserted therein.

FIGS. 1 and 11 illustrate the insertion of the elongate fluid coupling member 160 into the connector 110. As can be understood from reference to FIGS. 1, 10, and 11, the elongate fluid coupling member 160 is inserted through the passage 136, 148, 144, 146, 142 in the bushing seat 130 and bushing 140 respectively, and through passages 120, 125 such that passage 162 through the elongate fluid coupling member 160 is aligned with the passage 121 in the hose barb portion 114 of the connector body 112, or any other suitable connector formation integrally protruding therefrom. As the elongate fluid coupling member 160 is inserted, the retention flange 172 causes the flexible bushing 140 to flex therearound to establish substantially fluid-tight contact around the retention flange 172 as well as with other portions of the body portion 164 such that a substantially fluid-tight seal is established between the elongate fluid coupling member 160 and the bushing 140. Such arrangement also forms a frictional engagement between the elongate fluid coupling member 160 and the bushing 140 to retain the elongate fluid coupling 160 in coupled engagement therewith during normal use, yet permit easy detachment by grasping the connector body 112 and pulling it off of the elongate fluid coupling member 160. In addition, as can be most particularly seen in FIG. 11, when the elongate fluid coupling member 160 is seated within the bushing 140, the sealing ring 152 establishes a substantially fluid-tight seal with the bushing seat 130.

As can be further seen in FIG. 11, when the fluid coupling 160 is seated within the bushing 140 in this embodiment, the retention flange 172 is located a first distance "FD" from the end wall 113 of connector 112 and the seal ring 152 is located a second distance "SD" from the end 113. Also, bushing 140 may have a diameter "D" that is less than the diameter "D'" of passage 149 in bushing seat 130 and the bushing cavity 120 in the body portion 112. For example, the diameter "D" may be approximately 7.94 mm, for example, and the diameter "D'" may be approximately 8.75 mm, for example. See FIG. 10. Such arrangement may afford the bushing 140 with room to initially flex and expand as the elongate fluid coupling member 160 is inserted therein. In addition, by locating the seal ring 152 such that distance "FD" is less than "SD", the amount of stress placed on the seal ring 152 during insertion to the elongate fluid coupler 160 into the bushing 140 is reduced thereby increasing the life of the bushing 140 as well as reducing the amount of insertion force required to inserted the elongate fluid coupling member 160 into the bushing 140. However, in other embodiments, the seal ring 152 may be located such that "FD" is greater than "SD" as shown in FIGS. 12 and 13.

Figure 13:
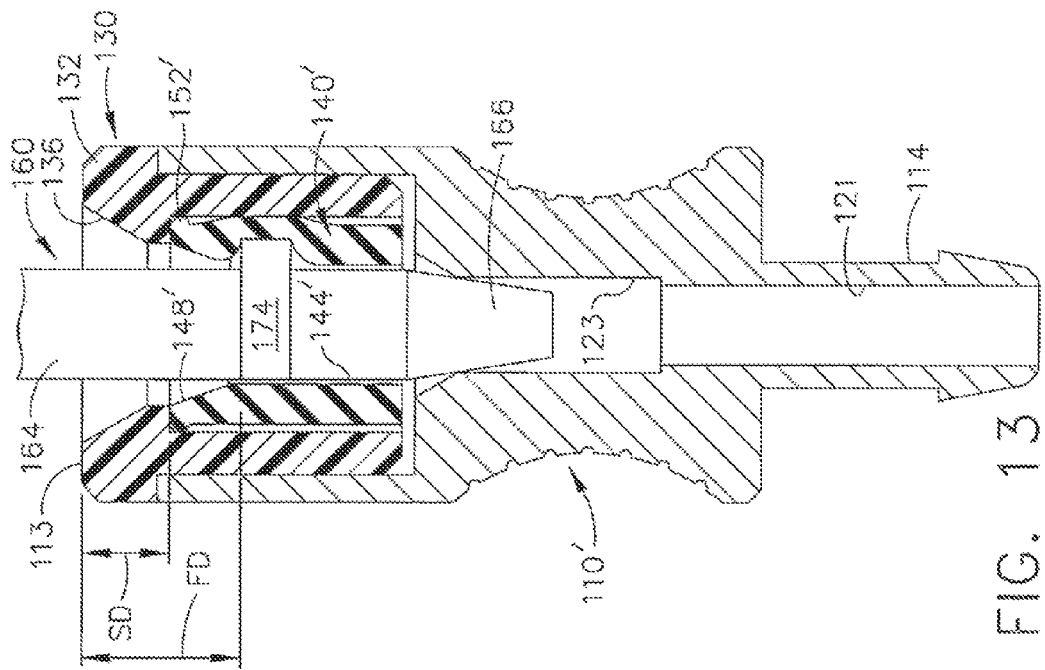
FIG. 13 is another cross-sectional view of the connector of FIG. 12 with an elongate fluid coupling inserted therein.
Figure 12:
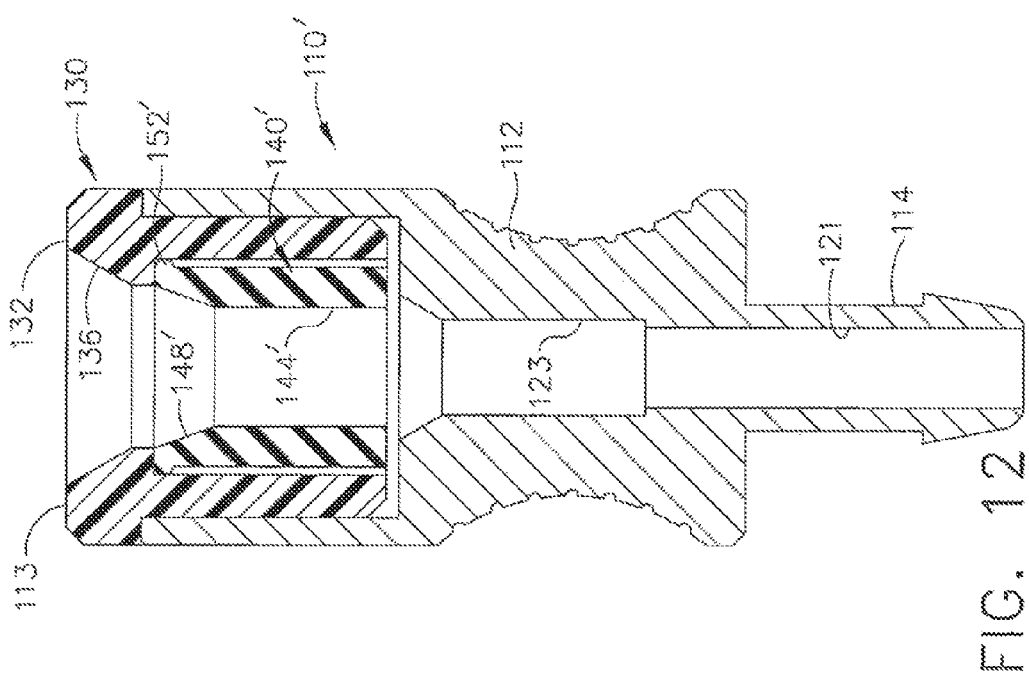
FIG. 12 is a cross-sectional view of an alternative connector embodiment of the present invention.

As can be seen in FIGS. 12 and 13, the bushing 140' is substantially similar to bushing 140 as described above, except for, among other things, the location of the sealing ring 152' and that the bushing 140 may be somewhat shorter than bushing 140'.

Thus, such arrangements have the advantage of being able to quickly couple adjacent ports on a medical instrument, such as an endoscope to a supply of fluid, such as a reprocessing unit without the use of tools and involved alignment procedures. Furthermore, although the embodiments disclosed herein have been described in connection with an endoscope, other embodiments are envisioned in connection with any suitable medical device.

Any patent, publication, application or other disclosure material, in whole or in part, that is said to be incorporated by reference herein is incorporated herein only to the extent that the incorporated materials do not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

The invention which is intended to be protected is not to be construed as limited to the particular embodiments disclosed. The embodiments are therefore to be regarded as illustrative rather than restrictive. Variations and changes may be made by others without departing from the spirit of the present invention. Accordingly, it is expressly intended that all such equivalents, variations and changes which fall within the spirit and scope of the present invention as defined in the claims be embraced thereby. While this invention has been described as having exemplary designs, the present invention may be further modified within the spirit and scope of the disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A connector assembly comprising:
a connector;
an elongate fluid coupling member, wherein said elongate fluid coupling member defines a longitudinal axis, wherein said elongate fluid coupling member comprises a substantially tubular portion extending along said longitudinal axis, and wherein an eccentric attachment feature is formed on said substantially tubular portion extending outward from said longitudinal axis, said connector comprising:
a connector body having an end wall and a bushing-receiving cavity therein, said end wall having a coupling opening therethrough sized to enable said substantially tubular portion to protrude therethrough; and
a flexible bushing received within said bushing-receiving cavity and having a passage therethrough to enable said substantially tubular portion and said eccentric attachment feature to be inserted within a proximal end of said passage, said flexible bushing sized relative to said bushing-receiving cavity to permit said bushing to flex therein about said eccentric attachment feature and said substantially tubular portion when said substantially tubular portion and said eccentric attachment feature are inserted into said proximal end of said passage in said flexible bushing, wherein said flexible bushing comprises a coupling member engagement surface configured to engage said elongate fluid coupling member and a bushing seat engagement surface comprising at least one seal feature protruding from said bushing seat engagement surface to establish a substantially fluid-tight seal between said bushing and a bushing seat, wherein said coupling member engagement surface comprises a proximal portion having a first diameter, wherein said coupling member engagement surface comprises an intermediate portion having a second diameter, wherein said coupling member engagement surface comprises a distal portion having a third diameter, wherein said first diameter is larger than said second diameter, wherein said second diameter is larger than said third diameter, and wherein said second portion of said coupling member engagement surface is configured to removably retain said substantially tubular portion and said eccentric attachment feature to establish a substantially fluid-tight seal between said connector and said elongate fluid coupling member.

2. The connector assembly of claim 1, wherein said at least one seal feature comprises at least one annular seal ring integrally formed in said bushing and protruding around a portion of a perimeter of said bushing.

3. The connector assembly of claim 1, wherein when said portion of said elongate fluid coupling member is seated within said bushing, said eccentric attachment feature is located a first distance from said end wall of said connector body and wherein said at least one seal feature on said bushing is located a second distance from said end wall of said connector body that is greater than said first distance.

4. The connector assembly of claim 1, wherein said flexible bushing is fabricated from approximately 50 Durometer Shore A silicone.

5. The connector assembly of claim 1, wherein said passage through said bushing has a tapered insertion portion.

6. A coupling arrangement for conveying a fluid through a medical device, said coupling arrangement comprising:
a substantially tubular elongate fluid coupling member in fluid communication with a channel extending through the medical device, said substantially tubular elongate fluid coupling member defining a longitudinal axis, said substantially tubular elongate fluid coupling member having at least one eccentric retention feature protruding therefrom;
a fluid conduit having a supply end operably communicating with a source of fluid and a discharge end;
a connector body attached to said discharge end of said fluid conduit, said connector body comprising:
an end wall;
a side wall protruding from said end wall and defining a cavity extending through said connector body; and
a coupling opening through said end wall such that at least a portion of said substantially tubular elongate fluid coupling member having said eccentric retention feature thereon may pass therethrough;
a bushing received within said cavity and having a passage therethrough sized to receive a portion of said substantially tubular elongate fluid coupling member and said at least one eccentric retention feature therein, said bushing having a length, wherein said bushing comprises a coupling member engagement surface configured to engage said substantially tubular elongate fluid coupling member and a bushing seat engagement surface, such that said substantially tubular elongate fluid coupling member and said at least one eccentric retention feature are removably retained within said bushing and a first substantially fluid-tight seal is established therebetween, wherein said coupling member engagement surface comprises a proximal portion having a first diameter, wherein said coupling member engagement surface comprises an intermediate portion having a second diameter, wherein said coupling member engagement surface comprises a distal portion having a third diameter, wherein said first diameter is larger than said second diameter, and wherein said second diameter is larger than said third diameter;
a bushing seat sized to receive said bushing therein; and
at least one seal feature extending from said bushing seat engagement surface for establishing a second substantially fluid-tight seal between said bushing seat and said bushing.

7. The coupling arrangement of claim 6, wherein said at least one seal feature comprises an annular seal ring integrally formed around a portion of a perimeter of said bushing.

8. The coupling arrangement of claim 6, wherein when said portion of said substantially tubular elongate fluid coupling member is seated within said bushing, said eccentric retention feature is located a first distance from said end wall of said connector body and wherein said seal feature on said bushing is located a second distance from said end wall of said connector body that is greater than said first distance.

9. The coupling arrangement of claim 6, wherein a portion of said bushing extending between said seal feature and said end wall of said connector body is sized relative to said cavity so as to permit said portion of said bushing to flex relative to said connector body during insertion of said substantially tubular elongate fluid coupling member and said at least one eccentric retention feature into said passage without compromising said second substantially fluid-tight seal formed between said seal feature and said connector body.

10. The coupling arrangement of claim 6, wherein said bushing is fabricated from approximately 50 Durometer Shore A silicone.

11. The coupling arrangement of claim 6, wherein said substantially tubular elongate fluid coupling member comprises:
a cylindrical body portion having a substantially circular cross-sectional shape and a fluid passage extending therethrough and said eccentric retention feature comprises a flange that protrudes eccentrically from said cylindrical body portion; and
a tapered discharge end protruding from said cylindrical body portion.

12. A coupling arrangement for conveying a fluid through a medical device, said coupling arrangement comprising:
an elongate fluid coupling member in fluid communication with a channel extending through the medical device, said elongate fluid coupling member comprises a cylindrical body portion extending along a longitudinal axis and an eccentric retention flange formed thereon, said eccentric retention flange extending outward from said longitudinal axis;
a fluid conduit comprising a supply end operably communicating with a source of fluid and a discharge end;
a connector body attached to said discharge end of said fluid conduit;
a bushing seat seated within said connector body, said bushing seat comprising a body portion and a flanged end, said body portion of said bushing seat comprising a bushing-receiving passage therethrough;
a flexible bushing having a length, said flexible bushing received within a cavity extending through said elongate fluid coupling member and said bushing-receiving passage in said bushing seat, said bushing comprising a passage therethrough sized to receive said cylindrical body portion of said elongate fluid coupling member therein such that said cylindrical body portion of said elongate fluid coupling member comprising said eccentric retention flange is removably retained within said bushing and a first substantially fluid-tight seal is established therebetween, wherein said bushing comprises a coupling member engagement surface configured to engage said substantially tubular elongate fluid coupling member and a bushing seat engagement surface, wherein said coupling member engagement surface comprises a proximal portion having a first diameter, wherein said coupling member engagement surface comprises an intermediate portion having a second diameter, wherein said coupling member engagement surface comprises a distal portion having a third diameter, wherein said first diameter is larger than said second diameter, and wherein said second diameter is larger than said third diameter; and
a seal for establishing a second substantially fluid-tight seal between said bushing seat and said bushing, wherein said seal extends from said bushing seat engagement surface.

* * * * *